United States Patent [19]
Kiel et al.

[11] Patent Number: 5,801,054
[45] Date of Patent: Sep. 1, 1998

[54] CELL CULTURE VESSEL WITH SELF-MAINTAINED ATMOSPHERE

[75] Inventors: Johnathan L. Kiel, Universal City; John L. Alls, San Antonio, both of Tex.

[73] Assignee: The United States of America as represented by the Secretary of the Air Force, Washington, D.C.

[21] Appl. No.: 716,691

[22] Filed: Sep. 19, 1996

[51] Int. Cl.$^6$ .................. C12M 3/00; C12M 1/24
[52] U.S. Cl. .................. 435/297.5; 435/286.6; 435/303.1; 435/304.3; 435/304.2
[58] Field of Search .................. 435/286.6, 287.6, 435/288.1, 288.2, 297.1, 297.5, 303.1, 303.2, 304.1, 304.3; 422/102; 206/213.1; 312/31; 215/261

[56] References Cited

U.S. PATENT DOCUMENTS

| | | | |
|---|---|---|---|
| 3,451,894 | 6/1969 | Anandam | 435/304.2 |
| 3,616,263 | 10/1971 | Anandam | 435/304.2 |
| 4,038,148 | 7/1977 | Miller et al. | |
| 5,047,347 | 9/1991 | Cline | 435/296 |
| 5,391,496 | 2/1995 | Kayal et al. | 435/304.3 |

FOREIGN PATENT DOCUMENTS

| | | | |
|---|---|---|---|
| 2 563 232 | 10/1985 | France | 435/303.2 |
| 25 11 622 | 9/1975 | Germany | 435/303.2 |
| 61-78373 | 4/1986 | Japan | 435/303.2 |
| 88/01605 | 3/1988 | WIPO | 435/304.3 |

Primary Examiner—William H. Beisner
Attorney, Agent, or Firm—Bobby D. Scearce; Thomas L. Kundert

[57] ABSTRACT

A cell culture device is described comprising a gas permeable vessel which contains one or more self contained carbon dioxide generators and which is attached to a closure closing a gas permeable cell culture flask. Located in the closure is a gas permeable insert which defines a gas permeable opening through which the gases from the atmosphere of the vessel produced by the carbon dioxide generators can communicate with the gases in the atmosphere of the flask. This invention allows the rapid and uniform equilibration of the atmosphere of the flask with the controlled atmosphere of the vessel while still providing a closed system which prevents the entry of microbial organisms into the flask. This invention provides a controlled atmosphere for up to 24 hours that maintains the pH of the culture medium for optimal growth of cells growing in the culture medium in the flask. This invention allows for continuous microscopic observation of cells during this period and for long term exposure of cells to various physical or chemical agents.

7 Claims, 3 Drawing Sheets

CELL CULTURE VESSEL WITH SELF-MAINTAINED ATMOSPHERE

FIELD OF THE INVENTION

The present invention relates generally to a cell culture device which provides a controlled atmosphere for long term cell culture.

BACKGROUND OF THE INVENTION

In vitro (outside a living organism) culturing of cells provides material needed for research in pharmacology, physiology, toxicology and radiation effects. The environmental conditions created for cultured cells should resemble as closely as possible the conditions experienced by the cells in vivo (in the body of a living organism). Although most cells will tolerate a hydrogen ion concentration (pH) range of 6.8 to 7.8, the optimal pH for growth of mammalian cells is 7.2–7.4. For the optimal pH to be maintained during cell cultivation, the cell culture medium must contain a buffering system.

Frequently, pH is maintained by using a bicarbonate buffering system in the medium, in conjunction with an incubator in which carbon dioxide ($CO_2$) is infused at a rate sufficient to maintain a concentration in the incubator atmosphere of approximately 5 to 7 percent volume. The carbon dioxide reacts with water to form carbonic acid which in turn interacts with bicarbonate ions ($HCO_3$) in the medium to form a buffering system which maintains the pH near physiologic levels. Entry of carbon dioxide from the incubator into the cell culture flask is generally achieved by using a loosely-fitting cap or stopper on the flask so that a small opening remains for the exchange of gas between flask and incubator. Alternatively, a gas permeable insert may be provided in the flask to allow the exchange of gases between the atmosphere of the culture flask and the atmosphere of the incubator in which the flask is placed for culturing. The gas permeable insert provides free passage of gases such as carbon dioxide while preventing passage of microbial organisms into the flask. U.S. Pat. No. 5,047,347, issued on Sep. 10, 1991, discloses such a gas permeable culture flask.

Removal of the flask from the controlled atmosphere of the incubator for long time periods is often required during growth and culturing of cells. The flasks are usually removed for observation or exposure to various physical and chemical agents. It is important that the pH of the cell culture be maintained at the desired physiological level while the flask is outside the incubator. Without maintenance of a proper carbon dioxide atmosphere, the pH level of the cell culture will rise. Within an hour, the medium will become alkaline and the cells will begin to decrease in mobility and undergo cell death.

Previously, to accomplish these long-time observations and exposures outside an incubator required frequent movement of culture flasks from the incubator to the microscope or exposure device and back to the incubator. Putting carbon dioxide into the flask and resealing the flask is another approach.

Special buffers that do not require a carbon dioxide atmosphere have also been used. Such special buffers include HEPES, tris, glycylglycine, and fee-base amino acids. However, these complex organic buffers could form free radicals that damage cells in culture or cause other chemical effects since they, unlike the bicarbonate/carbon dioxide buffering system described above, are not comparable to any natural buffering system.

All of these approaches cause disturbance of the cells interrupting the observations and metabolic stability of the cells.

OBJECTS OF THE INVENTION

It is, therefore, a principal object of the present invention to provide a culture device which includes features which provide a self maintained carbon dioxide atmosphere and allow for longterm observation and treatment of cells outside of an incubator without subjecting the cell culture to undesirable changes in the pH of the system or causing other undesirable chemical effects.

Another object of the present invention is to provide a cell culture device which includes features which allow for exposure of cells to desired levels of other gases such as nitrogen ($N_2$), hydrogen ($H_2$), oxygen ($O_2$), nitric oxide (NO) and other gases which are generatable or potentially generatable by a self contained gas generator. Self contained gas generators which generate gases other than carbon dioxide may be used in lieu of or in addition to, self contained carbon dioxide generators in order to study the effects of such gases upon the growth of the cell culture.

It is an advantage of the present invention that it provides for use of a buffering system that is representative of the natural in vivo buffering system.

Another advantage of the present invention is that sterility of the cells is more easily maintained because the invention is self contained.

A further advantage of the present system is that the cells are easily transported because the invention is a closed system; thus, the cells are less likely to be contaminated or lost during transport.

SUMMARY OF THE INVENTION

The present invention is directed to a cell culture device comprising a gas impermeable vessel which contains one or more self contained carbon dioxide generators and which is attached to a closure closing a gas impermeable cell culture flask. Located in the closure is a gas permeable insert which defines a gas permeable opening through which the gases from the atmosphere of the vessel produced by the carbon dioxide generators can communicate with the gases in the atmosphere of the flask. This invention allows the rapid and uniform equilibration of the atmosphere of the flask with the controlled atmosphere of the vessel while still providing a closed system which prevents the entry of microbial organisms into the flask. This invention provides a constant atmosphere for up to 24 hours that maintains the pH of the culture medium for optimal growth of cells growing in the culture medium in the flask. This invention allows for continuous microscopic observation of cells during this period and for long term exposure of cells to various physical or chemical agents.

Alternatively, self contained gas generators which generate gases other than carbon dioxide may be used in lieu of or in addition to, self contained carbon dioxide generators in order to study the effects of such gases upon the growth of the cell culture.

BRIEF DESCRIPTION OF THE INVENTION

DETAILED DESCRIPTION OF THE INVENTION

Figure 1:
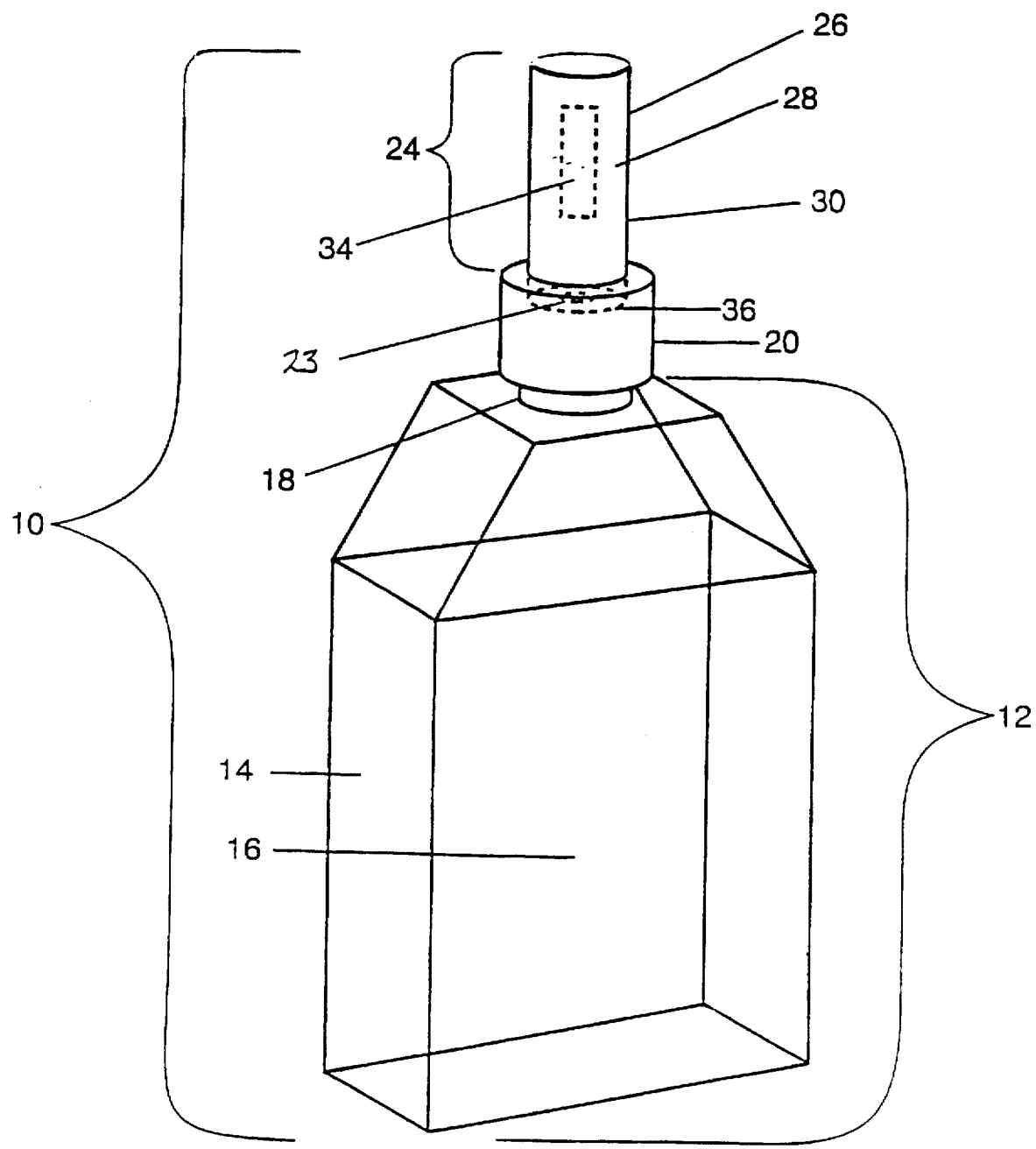
FIG. 1 is a perspective view of a preferred embodiment of the cell culture device in accordance with the present invention in which the vessel containing the self contained gas generators has one opening.

A preferred embodiment of a cell culture device with self-maintained atmosphere in accordance with the present invention is shown generally at 10 in FIG. 1. The culture device 10 includes flask 12 which is a conventional cell culturing flask which is preferably made from impact resistant plastic or glass which is gas impermeable, optically clear, non-toxic and inert with respect to the cells to be cultured. The flask 12 includes gas impermeable walls 14 which have a total surface area which can be determined from the dimensions of the flask being used. The flask walls 14 define a culturing zone 16. The culturing zone 16 will typically have an atmosphere containing one or more gases. The atmosphere within the culturing zone 16 prior to introduction of cells and culturing medium is usually air but may include other gases such as carbon dioxide, nitrogen or rare gases such as argon.

Figure 2:
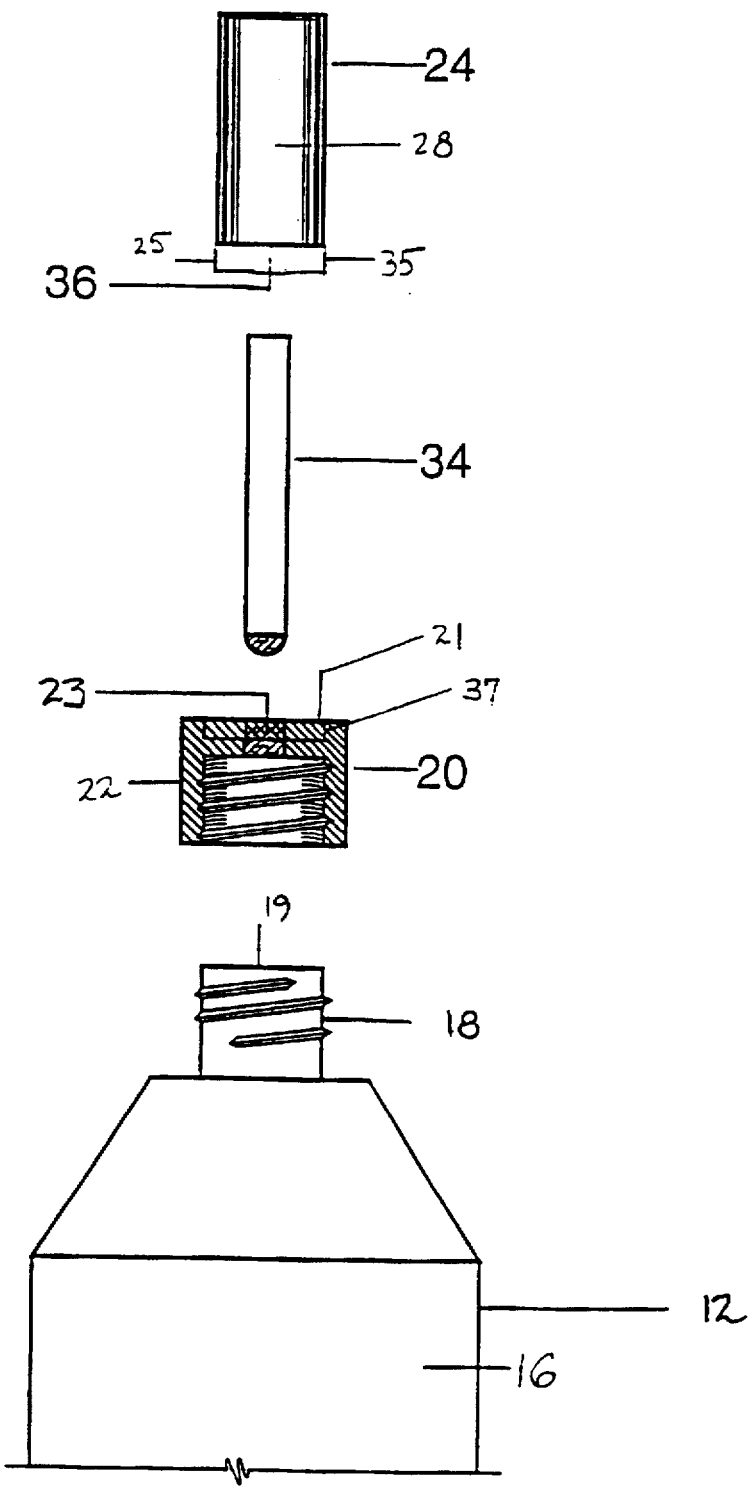
FIG. 2 is an exploded, longitudinal, axial, cross-sectional view of the culture device of FIG. 1.

The flask 12 includes a neck 18 which is threaded to receive a flask closure 20. As best shown in FIG. 2, the flask neck 18 is integral with the flask 12 and defines a cylindrical conduit having one end integral with the flask and the other end defining an opening 19 through which the cells and culture media may be introduced into the culturing zone 16. The flask closure 20 includes a top portion 21 with an annular skirt 22 extending therefrom. The flask neck 18 and the flask closure 20 constitute one of a number of well known means for introducing cells and culture media into culturing zone 16. As is conventionally known, the flask closure 20 is unscrewed from flask neck 18 to provide an opening 19 through which cells and culturing fluids can be introduced into the flask 12. The flask closure 20 is subsequently screwed back onto neck 18 to re-seal the flask 12.

In accordance with the present invention, a gas permeable insert 23 is provided in the top portion 21 of flask closure 20. The gas permeable insert 23 may be made from any suitable gas permeable material so long as it provides free passage of gases such as oxygen, nitrogen and carbon dioxide while preventing passage of microorganisms therethrough. Several gas permeable plastic materials having suitable pore size sufficient to permit free passage of oxygen and carbon dioxide while preventing passage of bacteria and fungi are available. These plastics include Celgard, a product of the Celanese Corporation and Nuclepore and Millipore GS membranes which are available from Nuclepore Corporation and Millipore Corporation respectively. The gas permeable plastic preferably will have an average pore size which is less than 0.2 microns, but not less than 0.01 microns. Plastics or other membrane materials with pore sizes within this range are preferred since they provide adequate rates of carbon dioxide and oxygen permeability while preventing passage of microorganisms.

As shown in FIG. 1, a particular feature of the present invention is a vessel 24 preferably made from impact resistant plastic or glass which is gas impermeable, optically clear, non-toxic and inert with respect to the cells to be cultured. The vessel 24 includes gas impermeable walls 26 defining a chamber 28. As best shown in FIG. 2, the vessel 24 includes a neck 35 which is integral with the vessel and defines a cylindrical conduit having one end integral with the vessel and the other end defining an opening 36 through which self contained gas generators 34 can be introduced into the chamber 28. Such a self contained gas generator is described in U.S. Pat. No. 4,038,148 issued on Jul. 26, 1977 and generally includes an ampule which contains a liquid which is reactive with a solid gas producing material. Upon rupture of the ampule, the liquid may be released to produce the desired chemical reaction to generate the desired gas. A self contained carbon dioxide generator consists of an ampule of dilute hydrochloric acid solution and a tablet of sodium bicarbonate. When the ampule is crushed, the tablet is activated producing carbon dioxide. Self contained carbon dioxide generators are available from Becton Dickinson Microbiology Systems.

The vessel neck 35 is removably mounted to the flask closure 20 allowing communication between the gases generated by the gas generators 34 in the chamber 28 and the gases in the culturing zone 16, such communication taking place through the gas permeable insert 23. The vessel neck 35 is mounted to the flask closure 20 by means of a groove 37 in the top portion of the flask closure 20. The groove 37 corresponds to the configuration of the vessel neck walls 25. The vessel neck walls 25 fit snugly into the groove 37, thereby covering vessel opening 36.

Figure 3:
FIG. 3 is a perspective view of a second preferred embodiment in which the vessel containing the self contained gas generators has two openings.
Figure 4:
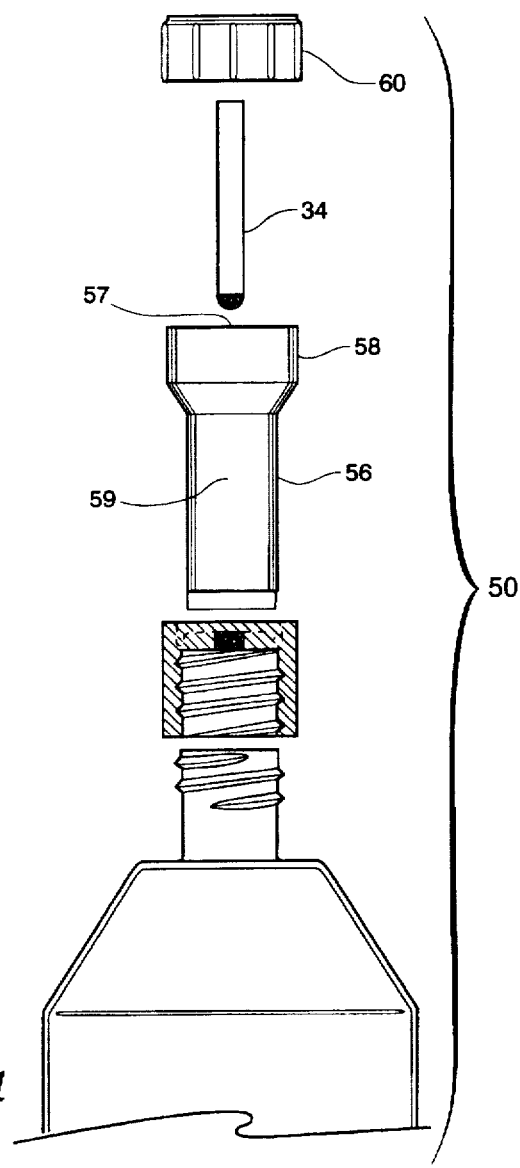
FIG. 4 is an exploded, longitudinal, axial cross-sectional view of the culture device of FIG. 3.

The cell culture device shown generally at 50 in FIG. 3 is an alternate preferred embodiment in accordance with the present invention. The vessel 56 is basically the same as vessel 24 shown in FIG. 1, except that vessel 56 also includes a second vessel neck 58 which is threaded to receive a vessel closure 60. The second vessel neck 58 is integral with the vessel 56 and defines a cylindrical conduit having one end integral with the vessel 56 and the other end defining an opening 57 through which the self contained gas generators 34 can be introduced into the chamber 59. As is conventionally known, the vessel closure 60 is unscrewed from second vessel neck 58 to provide an opening 57 through which the self contained gas generators 34 can be introduced into the chamber 28. The vessel closure is subsequently screwed back onto second vessel neck 58 to re-seal the vessel 56.

Having thus described exemplary embodiments of the present invention it should be noted by those skilled in the art that within disclosures are exemplary only and that various other alternatives, adaptations and modifications may be made within the scope of the present invention. Accordingly, the present invention is not limited to the specific embodiments as illustrated herein, but is limited only by the following claims.

We claim:

1. A cell culture device constructed for long-term treatment and observation of cells outside of a carbon dioxide incubator, said device having a self maintained atmosphere with selected levels of one or more gases including carbon dioxide gas, said gases generated by one or more self contained gas generators, said device comprising:

(a) a flask adapted for use in growing cell cultures, said flask having a unitary body including gas impermeable walls with a surface area defining a culturing zone having an atmosphere containing one or more gases;

(b) a neck connected to said flask body having an opening for introducing cells and culture fluids into said culturing zone to form a cell culture within said culturing zone;

(c) a closure for covering said opening in said flask neck, said closure comprising a top portion with an annular skirt extending from said top portion;

(d) means for removably mounting said closure to said flask neck whereby said closure may be removed from said flask neck when said cells and culturing fluids are to be introduced into or removed from said culturing zone;

(e) a gas permeable insert located in said flask closure defining a gas permeable opening through said closure, said gas permeable insert being made from material having a sufficiently large pore size to allow passage of said gases therethrough while having a sufficiently small pore size to prevent microorganisms from passing therethrough;

(f) a vessel having a unitary body including gas impermeable walls defining a chamber containing one or more self contained gas generators, said vessel body having a neck connected thereto, said vessel neck having gas impermeable walls and an opening for introducing said gas generators into said chamber, said vessel neck removably mounted to said top portion of said flask closure such that said vessel neck opening is covered by said top portion such that said gases from the atmosphere in said vessel produced by said gas generators can communicate with the gases in the atmosphere in said flask through said gas permeable opening to thereby allow equilibration between the two atmospheres to form an equilibrated atmosphere in said flask which is substantially equivalent to the atmosphere in said vessel, said atmosphere in said vessel having selected levels of one or more of said gases generated by said gas generators, said selected levels of said carbon dioxide gas being chosen to maintain optimum pH in said cell culture to provide the desired growth of said cell culture; and (g) means for removably mounting said vessel neck to said top portion of said closure whereby said vessel may be removed from said closure when said gas generators are to be introduced or removed from said chamber.

2. A cell culture device according to claim 1 wherein said means for removably mounting said closure to said flask neck includes a threaded portion on said flask neck and a mating threaded portion on said skirt of said closure to provide screw type mounting of said closure to said flask neck.

3. A cell culture device according to claim 1 wherein said means for removably mounting said vessel neck to said top portion of said closure includes a groove in said top portion of said closure, said groove corresponding to the configuration of said vessel neck walls such that said vessel neck walls fit snugly into said groove in said top portion of said closure.

4. A cell outside of a carbon dioxide incubator, said device having a self maintained atmosphere with selected levels of one or more gases including carbon dioxide gas, said gases generated by one or more self contained gas generators, said device comprising:

(a) a flask adapted for use in growing cell cultures, said flask having a unitary body including gas impermeable walls with a surface area defining a culturing zone having an atmosphere containing one or more gases;

(b) a neck connected to said flask body having an opening for introducing cells and culture fluids into said culturing zone to form a cell culture within said culturing zone;

(c) a flask closure for covering said opening in said flask neck, said flask closure comprising a top portion with an annular skirt extending from said top portion;

(d) means for removably mounting said flask closure to said flask neck whereby said flask closure may be removed from said flask neck when said cells and culturing fluids are to be introduced into or removed from said culturing zone;

(e) a gas permeable insert located in said flask closure defining a gas permeable opening through said closure, said gas permeable insert being made from material having a sufficiently large pore size to allow passage of said gases therethrough while having a sufficiently small pore size to prevent microorganisms from passing therethrough;

(f) a vessel having a unitary body including gas impermeable walls defining a chamber containing one or more self contained gas generators, said vessel body having a first neck connected thereto, said first vessel neck having gas impermeable walls and an opening therethrough, said first vessel neck removably mounted to said top portion of said flask closure such that said first vessel neck opening is covered by said top portion such that said gases from the atmosphere in said vessel produced by said gas generators can communicate with the gases in the atmosphere in said flask through said gas permeable opening to thereby allow equilibration between the two atmospheres to form an equilibrated atmosphere in said flask which is substantially equivalent to the atmosphere in said vessel, said atmosphere in said vessel having selected levels of one or more of said gases generated by said generators, said selected levels of said carbon dioxide gas being chosen to maintain optimum pH in said cell culture to provide the desired growth of said cell culture;

(g) means for removably mounting said first vessel neck to said top portion of said flask closure;

(h) a second vessel neck connected to said vessel body having an opening for introducing said gas generators into said chamber;

(i) a vessel closure for covering said opening in said second vessel neck; and (j) means for removably mounting said vessel closure to said second vessel neck whereby said vessel closure may be removed from said second vessel neck when said gas generators are to be introduced or removed from said chamber.

5. A cell culture device according to claim 4 wherein said means for removably mounting said flask closure to said flask neck includes a threaded portion on said flask neck and a mating threaded portion on said flask closure to provide screw type mounting of said flask closure to said flask neck.

6. A cell culture device according to claim 4 wherein said means for removably mounting said first vessel neck to said top portion of said flask closure includes a groove in said top portion of said flask closure, said groove corresponding to the configuration of said vessel neck walls such that said vessel neck walls fit snugly into said groove in said top portion of said flask closure.

7. A cell culture device according to claim 4 wherein said means for removably mounting said vessel closure to said second vessel neck includes a threaded portion on said second vessel neck and a mating threaded portion on said vessel closure to provide screw type mounting of said vessel closure to said second vessel neck.

* * * * *